United States Patent
Dutto et al.

(10) Patent No.: US 6,374,133 B1
(45) Date of Patent: Apr. 16, 2002

(54) EXAMINATION TABLE, PARTICULARLY IN MACHINES FOR NUCLEAR MAGNETIC RESONANCE IMAGE DETECTION

(76) Inventors: Roberto Dutto, Viale Mojon 3/2, I-16122 Genoa; Orfeo Contrada, Via Cherubini 8/61, I-16159 Genoa; Fabio Rezzonico, Via A. Diaz 14, I-22100 Como, all of (IT)

( * ) Notice: Subject to any disclaimer, the term of this patent is extended or adjusted under 35 U.S.C. 154(b) by 0 days.

(21) Appl. No.: 09/986,169

(22) Filed: Nov. 7, 2001

Related U.S. Application Data

(62) Division of application No. 09/141,260, filed on Aug. 27, 1998.

(30) Foreign Application Priority Data

Sep. 16, 1997 (IT) .......................................... SV97A0040

(51) Int. Cl.⁷ .............................................. A61B 5/055
(52) U.S. Cl. ............................... 600/415; 5/601; 5/623; 5/624; 324/318
(58) Field of Search ................................ 600/410, 415; 5/601, 613, 621–624; 378/208, 209; 324/307, 309, 318

(56) References Cited

U.S. PATENT DOCUMENTS

| | | | |
|---|---|---|---|
| 4,589,126 A | 5/1986 | Augustsson et al. | |
| 4,681,308 A | * 7/1987 | Rice | 5/601 |
| 5,008,624 A | 4/1991 | Yoshida | |
| 5,305,749 A | * 4/1994 | Li et al. | 600/415 |
| 5,735,278 A | 4/1998 | Hoult et al. | |
| 5,986,531 A | * 11/1999 | Carrozzi | 600/415 |
| 6,141,579 A | * 10/2000 | Bonutti | 600/415 |

FOREIGN PATENT DOCUMENTS

JP 01-209053 8/1989

* cited by examiner

*Primary Examiner*—Ruth S. Smith
(74) *Attorney, Agent, or Firm*—Burns, Doane, Swecker & Mathis, L.L.P.

(57) ABSTRACT

A method of imaging a part of a body with a nuclear magnetic resonance image forming machine designed for forming imaging of only parts of a body, in combination with an examination table, wherein there is a guide for moving the examination table to and from the machine in a line, and wherein the examination table is able to rotate along a vertical rotational axis. The method includes the steps of arranging a patient on the table so that the part of the body to be imaged extends off table, orienting the table about the vertical rotational axis so that the part of the body to imaged extends along the line, moving the table toward the machine until the part of the body to be imaged is in a detection cavity of the machine and while all of the table is outside of the detection cavity, and forming an image of the part of the body with the machine.

11 Claims, 9 Drawing Sheets

EXAMINATION TABLE, PARTICULARLY IN MACHINES FOR NUCLEAR MAGNETIC RESONANCE IMAGE DETECTION

CROSS-REFERENCE TO RELATED APPLICATIONS

The present application is a divisional application of Ser. No. 09/141,260, filed on Aug. 27, 1998, the entire contents of which is hereby incorporated herein by reference.

BACKGROUND OF THE INVENTION

1. Field of the Invention

The invention relates to an examination table, particularly in Nuclear Magnetic Resonance image detecting machines of the so-called dedicated type, i.e., designed for detecting images of specific body parts.

2. Discussion of Related Art

Currently, in the so-called dedicated Nuclear Magnetic Resonance image detecting machines, i.e., those designed for detecting images of specific body parts, and having an image detection cavity of such a size as to prevent the insertion of the whole body (like in the so-called total-body machines), the patient is asked to sit or lay down on a chair or on an examination table. The latter are of the conventional type, and have no particular construction characteristics to comply with specific functions, examinations and corresponding positions of the patient with respect to the machine and to the detection cavity. Therefore, prior art examination tables and chairs are not only very complex and expensive, in order to ensure that the patient always has the right position with respect to the detection cavity, but are also uncomfortable and inconvenient for patient positioning. The high costs and the uncomfortable and time-consuming positioning operations required by prior art equipment are the most significant drawbacks thereof.

OBJECTS AND SUMMARY

The invention has an object to provide an examination table of the type described hereinbefore, which allows, by simple and inexpensive arrangements, for easy and fast patient positioning operations, requiring a minimum number of adjustments, without affecting the comfort of the patient during the image detection process.

The invention achieves the above objects by providing an examination table of the type described hereinbefore, which is included in dedicated machines for detecting Nuclear Magnetic Resonance images of specific body parts, and wherein the examination table has an at least one-degree-of-freedom constraint to the image detection machine, and has support means which allow the examination table to be moved in at least one, preferably two or more degrees of freedom.

In a preferred embodiment, the examination table is mounted is such a way as to be able to slide on a stationary guide, which is fixed with a predetermined orientation with respect to the detection cavity of the machine, and it may be further translated in both senses along said guide and rotated about an axis perpendicular to the direction it follows while sliding on the guide.

Particularly, the rectilinear translation guide is oriented in the direction of insertion/extraction of one part of the patient body in or from the detection cavity by a simple straight-line translation movement, while the examination table may be also rotated about an axis perpendicular to said translation direction.

Especially, the rectilinear guide is horizontal, while the axis of rotation of the examination table is vertical.

The examination table advantageously has three points of support, i.e., two wheels, at two corners of one end side thereof, said wheels being also rotatable about a vertical axis, and another point of support, coinciding with a vertical axis of rotation which corresponds to the median longitudinal axis at the opposite end side of the examination table.

The vertical axis of rotation is provided at the top of a supporting column, which has a lower carriage with at least three points of support, i.e., at least one central sliding wheel, associated to the guide, and at least two lateral wheels, touching the ground, and being also rotatable about a vertical axis.

Advantageously, there are provided at least two wheels associated to the guide, one behind the other in the median vertical plane of the examination table.

According to a further characteristic, the examination table has a stationary part, whose length substantially corresponds to the average length of the trunk, and an overturning extension, provided at one end, having the function of a footrest. The footrest may be overturned into a projecting position, in which it extends the examination table, and into a rest position, in which it is substantially parallel to, or possibly partially hidden in the corresponding end side of the examination table.

The examination table is anatomically curved, the curved region being moved towards the end side with the two wheels, i.e., in the area intended to receive the pelvis.

In the pelvis area, i.e., in the curved region, there is provided one removable armrest for each side.

The vertical axis of rotation of the examination table, corresponding to the third point of support thereof, is provided in the region associated to the upper back.

The substantially plane back-supporting area extends with a predetermined inclination with respect to the wholly horizontal orientation, i.e. with a rising inclination from the lowest zone of the hollow formed by the curve.

The opposite, much shorter branch, associated with legs, and provided with the overturning footrest, is also oriented with a certain rising inclination towards the end side of the examination table associated thereto.

Thanks to the arrangements described above, the examination table according to the invention has a very simple, stout, safe, comfortable and cost-effective construction. The parts to be jointed to the examination table are only the footrest, the wheels and the vertical axis of rotation. By connecting the examination table to the machine through the horizontal rectilinear rail, the approaching motion of the patient towards the machine, and the insertion of the limb to be examined therein, may be limited to a single degree of freedom, i.e. to a translation movement in said direction of insertion/extraction of the limb in and from the detection cavity.

Patient positioning, for performing examinations of different limbs, particularly arms and legs, may be obtained by simply rotating the examination table about the vertical axis.

The examination table according to the invention is particularly provided in combination with a Nuclear Magnetic Resonance image detecting machine having a tubular detection cavity, i.e. of the type for alternatively detecting images of different parts of a leg and foot, and of an arm and hand. Here, the construction described above is notably advantageous. The guide and hence the translation movement of the examination table in the direction of insertion/ extraction of the body part in and from the detection cavity are oriented parallel to the axis of the tubular detection cavity and are contained in the vertical plane also containing the central axis thereof. In order to examine one leg or one arm, for example a knee or a foot and one hand, a simple rotation of the examination table is needed, in the first case with the longitudinal axis parallel to the translation direction, and in the second case in one of the two opposite positions transverse, particularly perpendicular to the translation direction. Further, the overturning footrest allows the patient to take a sufficiently comfortable position, so that he can keep the part under examination still, be it a part of an arm or of a leg. During the examination of arm parts, the footrest may be turned outwardly into the operating position, while, in order to examine a leg part, especially a knee, it must be turned into the retracted position, substantially flush with the examination table end facing the detection cavity. In this way, the examination table may be approached to the cavity to the extent required to bring the knee in the imaging zone, without forcing the patient to take an uncomfortable position.

BRIEF DESCRIPTION OF THE DRAWINGS

The characteristics of the invention and the advantages derived therefrom will appear more clearly from the following description of an embodiment, illustrated by way of a non-limiting example in the accompanying drawings, in which.

DETAILED DESCRIPTION OF THE PREFERRED EMBODIMENTS

Figure 1:
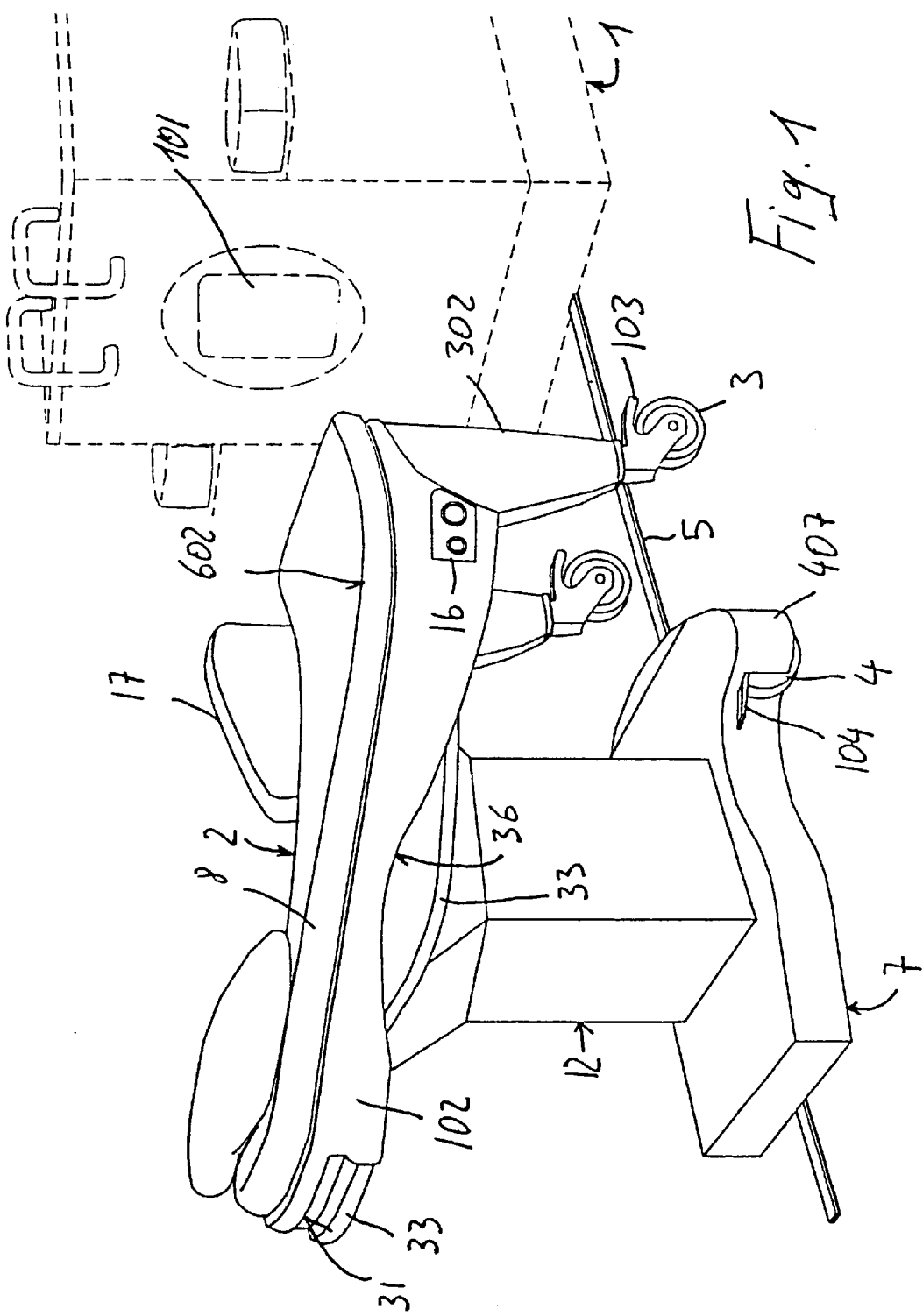
FIG. 1 is a schematic perspective view of a Nuclear Magnetic Resonance imaging machine, with an examination table according to the invention.

With reference to the annexed figures, a Nuclear Magnetic Resonance Image detecting machine 1, of the type designed for detecting images of specific body parts or limbs, like a leg, a knee, a foot, an elbow, a hand, an arm, etc. has a tubular detection cavity 101, wherein the limb or the body part, i.e., the arm or the leg, are inserted in a direction parallel or approximately parallel to the axis of the tubular detection cavity 101. See FIG. 1. Hence, in these machines, the patient is always meant to stay outside the image detection cavity 101. In combination with the machine, there is provided an examination table 2, which is mounted in such a way as to be able to slide on wheels 3, 4 on a translation guide 5 which is integral with the machine 1, and oriented towards the axis of the tubular detection cavity 101, preferably and particularly being contained in the vertical plane which passes through the central axis of said detection cavity 101. The guide 5 has a predetermined length and is shaped so as to ensure that the shoes, or particularly the accordingly shaped rollers 6, which are provided in a corresponding position in a carriage 7 of the examination table, do not perform transversely staggered movements, but only one translation movement longitudinal to the guide.

Figure 6:
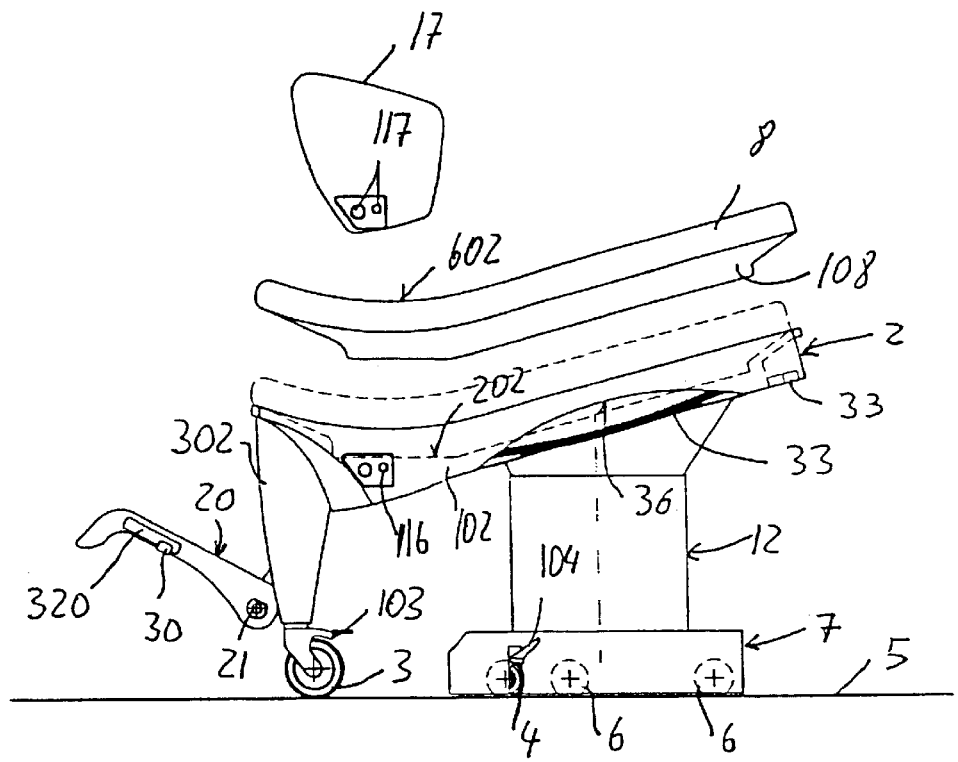
FIG. 6 is an elevational side view of the examination table according to the previous figures, with the mattress and one armrest being detached therefrom.
Figure 7:
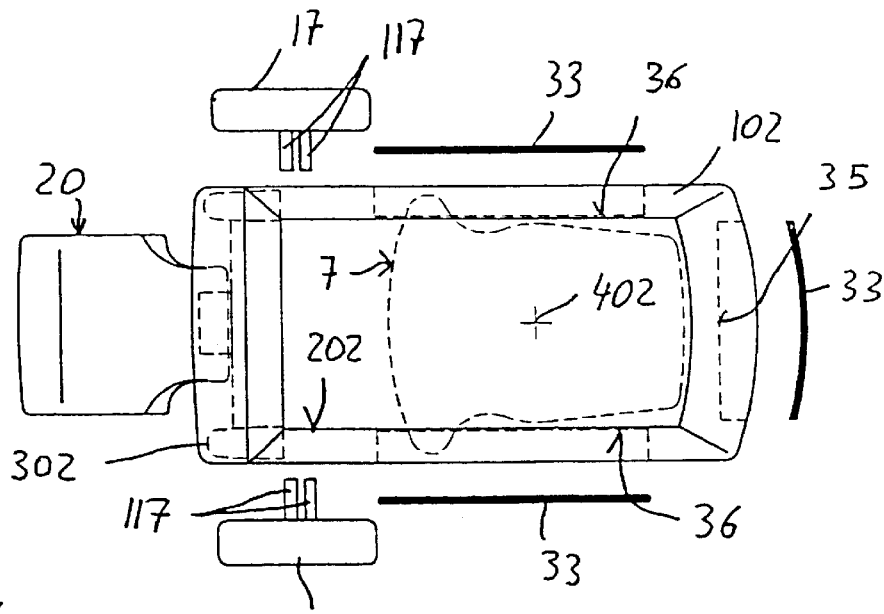
FIG. 7 is a top plan view of the examination table according to FIG. 6, with the two armrests being detached therefrom and set up for mounting.
Figure 8:
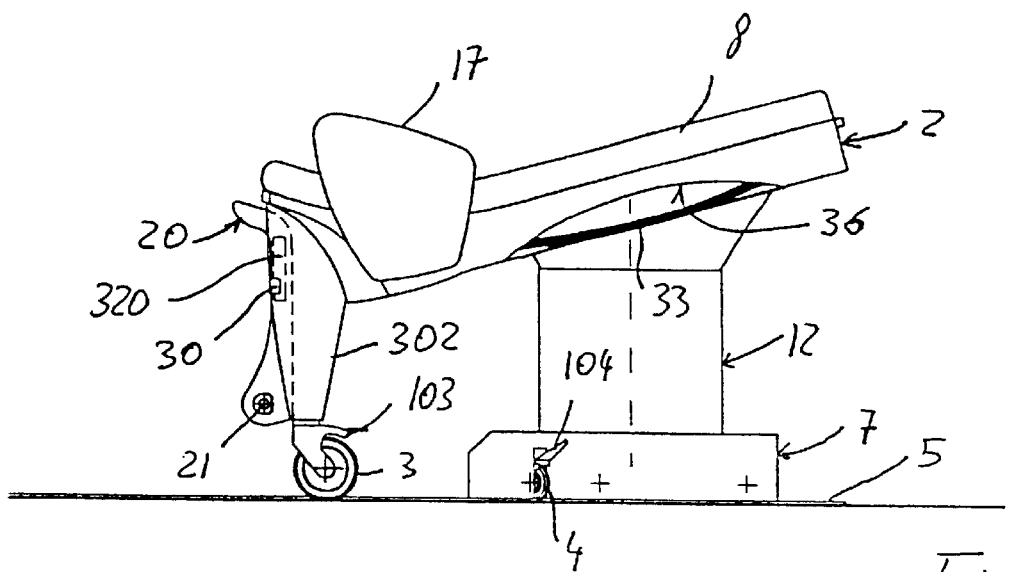
FIGS. 8 and 9 are elevational side views of the examination table with the footrest in the idle and operating positions respectively.
Figure 9:
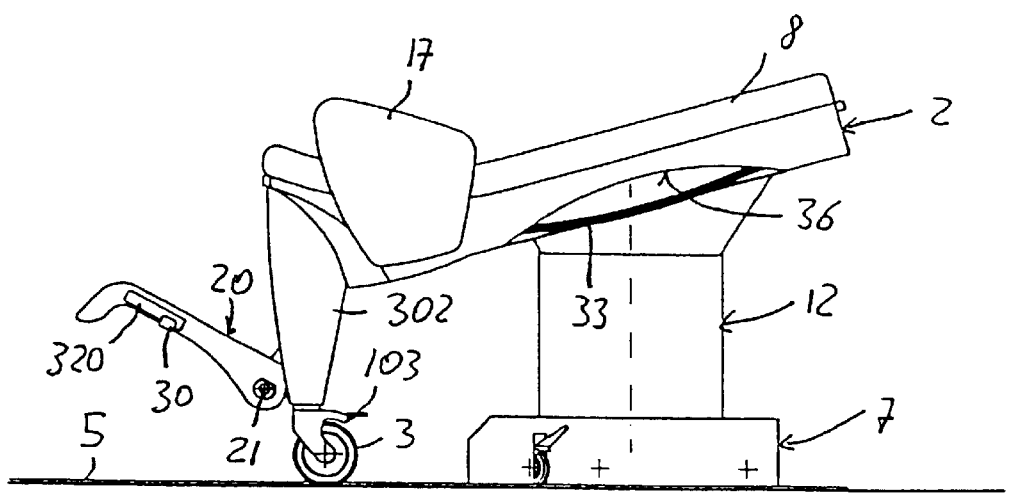
Figure 10:
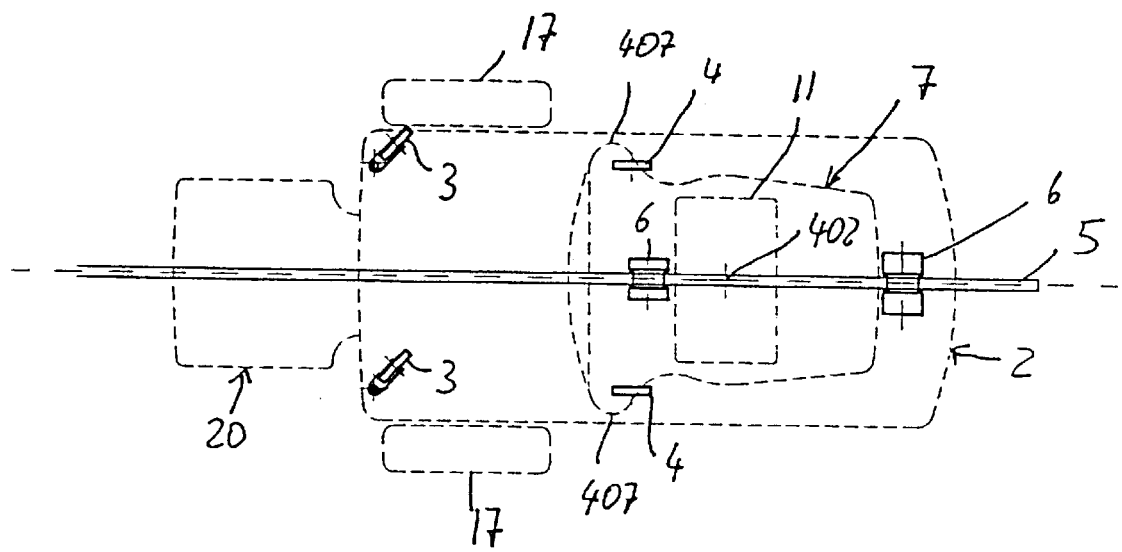
FIG. 10 is a schematic view of the wheels used for sliding along the translation guide which is integral with the machine.

The examination table consists of a supporting plane 102, having an upper hollow, in the form of a tub 202, of the type which flaringly tapers towards the bottom, and being meant to receive a rear projection, accordingly flared 108, of a mattress 8, there being provided removable means for fastening the mattress 8 to the supporting plane 102. These means may be of any type, for example in the form of snap fasteners, or consisting of fastening tapes of the type known under the name of VELCRO fasteners, or similar fasteners. See FIGS. 6 and 7.

The total height of the examination table substantially corresponds to the height of the lower side of the detection cavity 101, there being provided that position tolerances with respect to height are positively uncritical for patient positioning, so that the patient is always able to introduce the limb to be examined into the detection cavity 101, while being in a lying position.

The bearing plane 102 and, accordingly, the mattress 8 are concave, with the axis of curvature being transverse to the longitudinal extension of the examination table, and with the lower and curved zone being provided closer to one of the two examination table ends 2, i.e., the one which will be referred to, hereafter and in claims, as the feet end. In the direction of the feet end, and of the end being opposite thereto, referred to as the head end, the bearing plane 102 and the mattress 8 are substantially straight, or slightly concavely curved, and are anyway oriented on a plane which is inclined with respect to the horizontal plane, in a rising direction towards the associated end. The examination table 102 has such a length that the feet end terminates substantially on the same level as a statistically intermediate point of the leg, particularly between the knee and the trunk. Obviously, the patient may be positioned either slightly staggered with respect to the feet end, or slightly staggered with respect to the head end, according to the type of limb to be examined.

The feet end has two vertical legs 302, each having, at its end, a wheel 3, provided with brakes 103, and rotatable not only about a horizontal axis, but also about a vertical axis. See FIG. 1.

In the zone associated with the head end, the examination table, i.e., the plane 102 is supported by a fulcrum, which coincides with the longitudinal median axis thereof, and around which the plane 102 may rotate about a vertical axis 402. This may be obtained thanks to two horizontal or substantially horizontal plates 9, 10, which are connected in such a way as to be in mutual rotation about one intermediate point, which is substantially perpendicular thereto. An upper plate 10 is attached to the lower side of the bearing plane 102, or to a flange associated thereto, by means of a wedge-shaped spacer 11, which acts as a support, whose inclination corresponds to that provided for the bearing plane 102 in said attachment point. The other plate, the lower plate 9 is carried at the top of a vertical column 12, extending upwards from a lower carriage 7.

Figure 11:
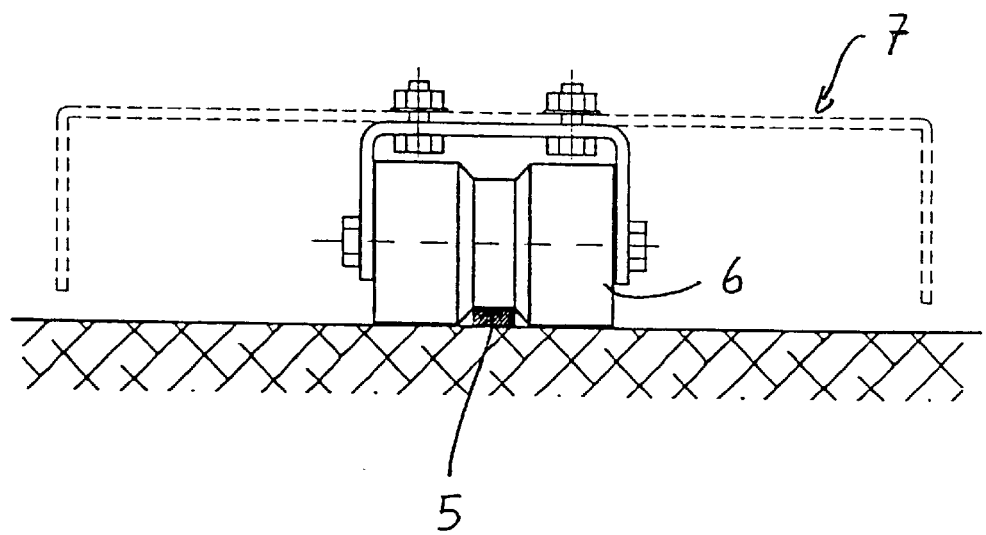
FIG. 11 is a view of a wheel as seen in the direction of the translation guide.
Figure 13:
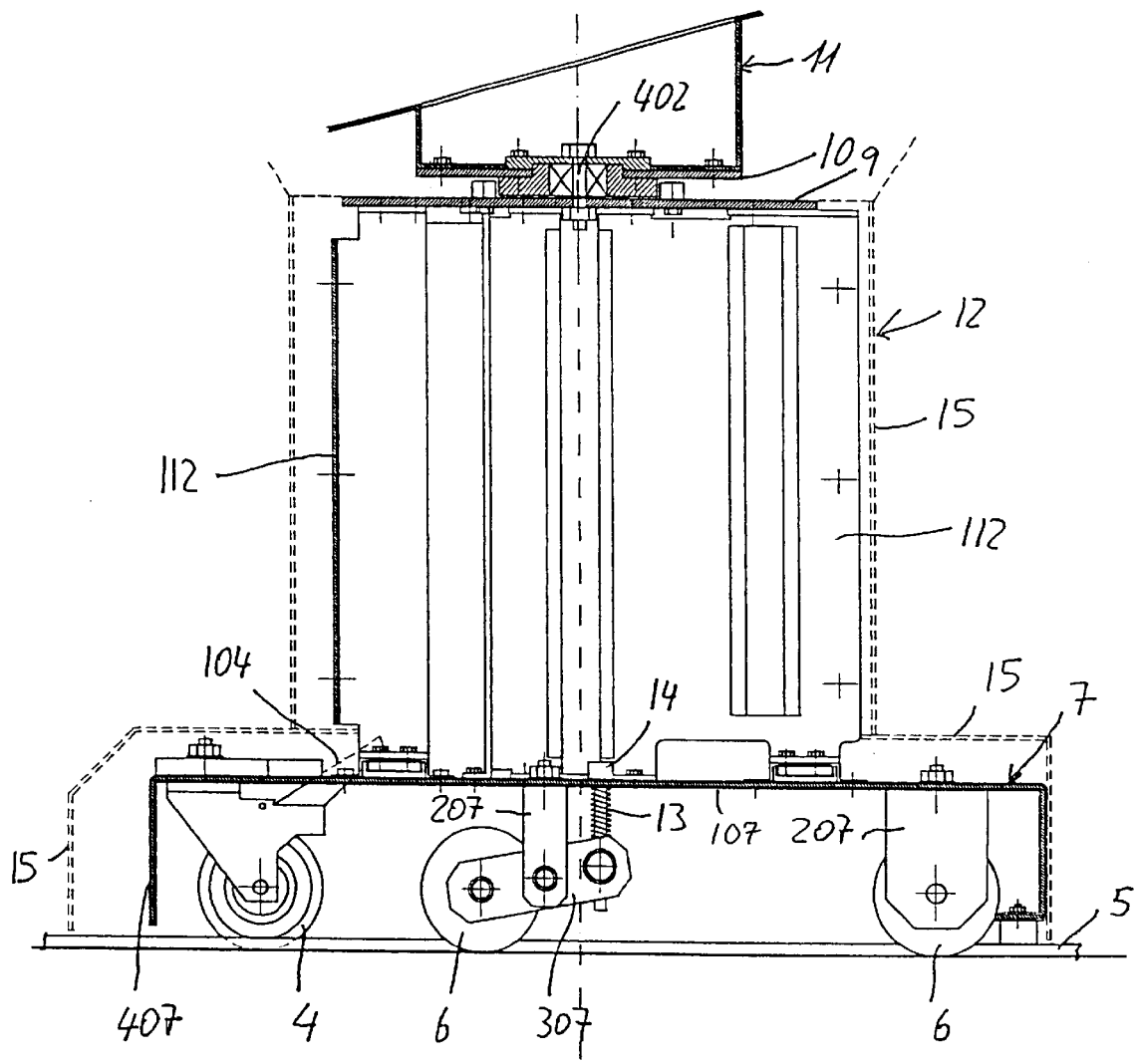
FIG. 13 is a sectional view of the examination table end, associated to the head, as taken across the rotatable support column.
Figure 14:
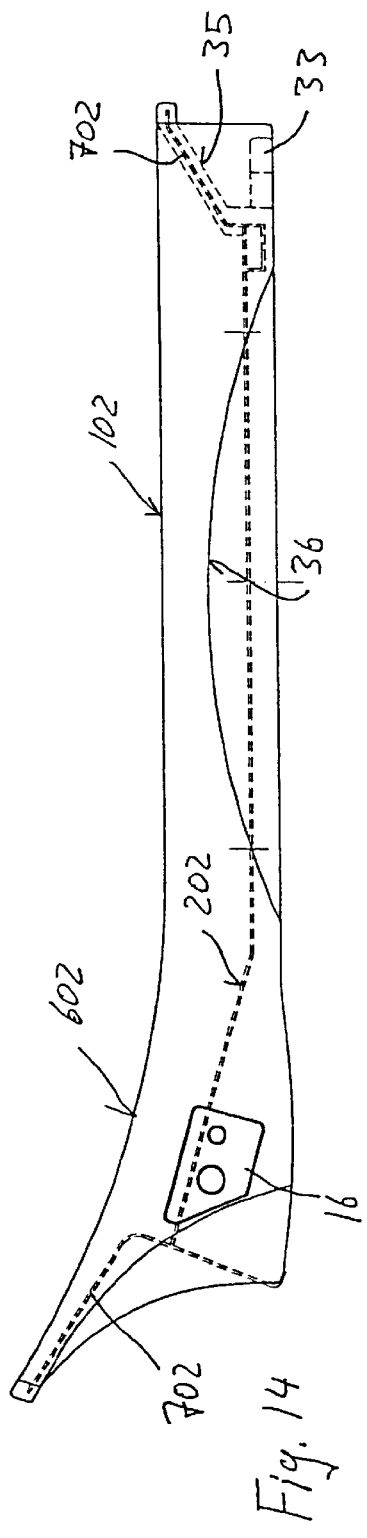
FIGS. 14 and 15 are top and magnified side views respectively of the other construction details of the examination table and of the bearing strengthening structure thereof, outlined by dashed and dotted lines.
Figure 15:
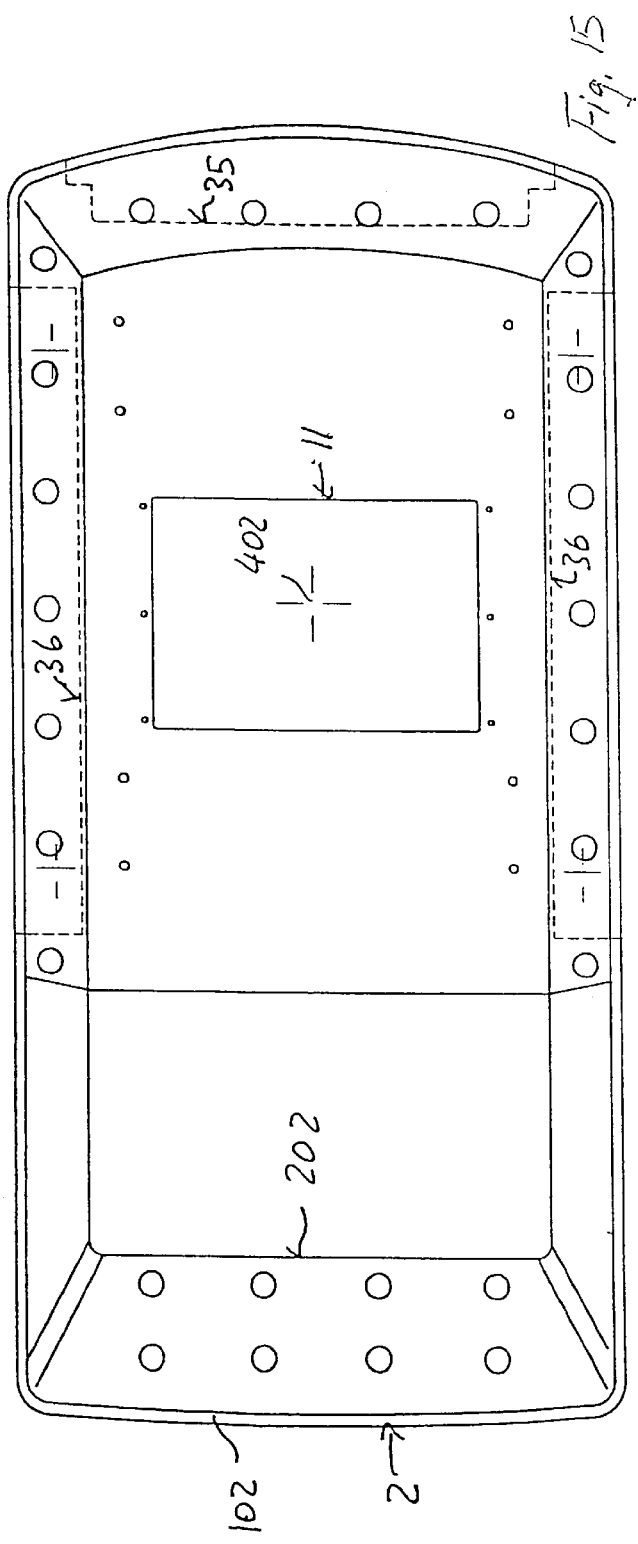

The carriage 7 has two successive translation rollers 6 in the median area and in line along the guide 5, said rollers 6 being shaped so as to be complementary to the cross section of the guide. See FIG. 11. The rollers 6 are supported, by an upper plate 107 of the carriage 7 through forks 207. The rollers 6 may be also elastically supported by elastic means, for example springs 13, interposed between a support bracket 307, for example an equalizer or a bracket being able to swing or slide vertically and a matching member, integral with the plate 107. The springs 13 may be associated with means 14 for adjusting their preloading state, for example screw means for generating a certain precompression of the swinging arm 307 on the spring 14. See FIG. 13.

The carriage 7 also has two transverse wings 407, which are substantially symmetrical with respect to the longitudinal median axis, each one bearing, at a certain distance from said axis and symmetrically thereto, one wheel 4, which is to touch the ground and to rotate both about a horizontal axis and about a vertical axis. The wheels 4 may be also provided with braking or locking means 104.

The bearing plane 102, the carriage 7 and the column 12 all have a construction provided with an inner load bearing core, for example made of metal, like sheet metal, or similar, or of any material suiting its mechanical characteristics, said core having mounts 112 for fastening coverings or cases 15, made of a material unfit for bearing structures. Hence, finishing operations are greatly simplified thanks to this substantially modular structure. So, for example, the bearing plane of the examination table also has a load bearing core 702, only shown by way of indication, which is covered by a case, providing it with the desired exterior shape.

In the hollow area 602, being designed to receive the pelvis, the bearing plane 102 has one mount on each side, for one armrest 17 respectively. The armrests 17 consist of elements having an approximately trapezoid shape, when seen in a side view. The means for removable attachment thereof to the plane 102 of the examination table 2, consist of a pair of transverse pins 117, which are meant to engage in holes 116 matching the pins 117 the sides of the plane 102 of the examination table. One pin, being radially larger, acts as a support pin, and the other has the function to prevent the armrest 17 from rotating about the support pin.

A footrest 20 is attached to the two legs 302 at the corners of the examination table end, associated with feet. The footrest is supported so as to turn about a horizontal axis, between at least one outwardly projecting operating position, and an idle position, in which it is substantially parallel to the plane subtended by the two legs 302 of the examination table, or may be even retracted so as to be hidden in a recess formed between the two legs, and partially in the two legs 302, appropriately shaped.

The footrest 20 is hinged about a horizontal axis, transverse to the longitudinal axis of the examination table 2, and located at an intermediate height between the ground and the plane 102. The height of the hinging axis is chosen in such a way that the patient may have his trunk laid, while the lower part of the leg, from the knee down, is substantially vertical and the foot rests on the footrest 20. This allows the patient to be in a relatively comfortable and stable position, i.e. with his body on the same axis as the detection cavity 101, when images of a foot region, or of the leg region below the knee are to be detected. Conversely, in order to detect images of the knee, the footrest 20 is turned to the idle position, allowing the examination table 2 to get closer to the machine 1, while the leg under examination rests on the structure of the machine 1, and the other leg is kept slightly bent in a relatively comfortable position, forming an inverted V, with the knee up, or kept sideways, in said inverted V position.

Obviously, the vertical position of the hinging axis may be easily adjustable, by providing that the hinge is mounted on a sliding saddle, and that it may be locked in its position in two lateral guides, each fixed to a leg 720.

In most cases, by setting the height of the hinging axis of the footrest 20 to the average body size of patients, the hinging axis may be fixed, as in the present example.

Figure 12:
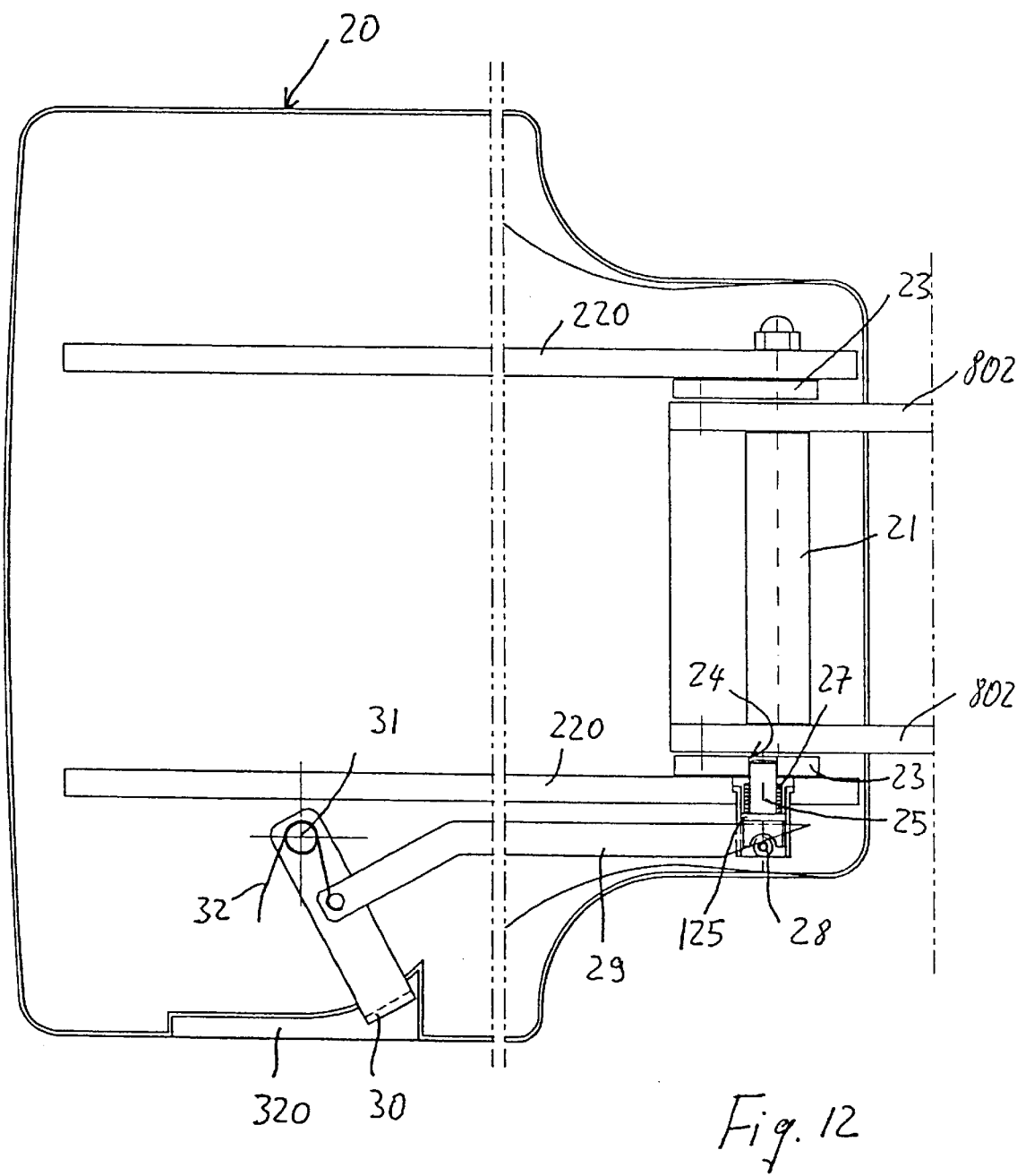
FIG. 12 shows a detail of the overturning footrest.

Referring to FIG. 12, the footrest 20 has a central extension 120, forming a first fork 220, on the side designed to be jointed. The first fork 220 has, on its two branches, two through holes, for the passage of a horizontal and transverse hinging pin, which passes through coincident holes formed on the two branches of a second fork 802, projecting out of the examination table end 102, and whose branches superpose the inner faces of the two branches of the first fork 220. Between the branches of the second inner fork 802 and those of the first outer fork 220, there are provided two plates 902. The latter have means for attachment to the branches of the second fork 802, for example pins or pegs, schematically shown by their axis, indicated as 23, the hole for the passage of the hinging pin 21 and a hole 24, at a predetermined radial and angular distance from the hinging axis 21, for engaging a locking tooth or pin 25, which is alternately movable in the axial direction of the hole 24 to a position in which it is retracted from the hole 24 and to a position in which it is engaged in the hole 24, said engagement position corresponding the footrest 20 being locked in the outwardly overturned operating position.

The locking pin 25 is slidably supported in a tubular guide 26, integral with the corresponding branch of the first fork 220, and is subject to the action of an elastic member, preferably a spring 27, which stably pushes it into the position in which it is retracted from the hole 24, and against a retraction end-of-stroke matching member 28. The latter extends beyond the diameter of the pin and forms, together with an annular enlarged wall, a guide for a driving rod 29, which has, at its free end, a wedge-shaped surface having the function of a cam 129. When the rod 29, together with the wedge-shaped cam 129, slides transverse to the axis of the locking pin 25, it causes the pin to move to the position in which it is engaged in the hole 24, against the action of the spring 27. The rod 29 extends up to the lateral area of the footrest 20, which is shaped like a box, and the end opposite to the cam 129 is jointed into an intermediate point of an operating lever 30, whose fulcrum 31 corresponds to its end inside the footrest 20, whereas it projects by a driving button or shaped end, at its free end, into a lateral niche 320 of the footrest 20. The lever 30, and thereafter the rod 29 and the cam 120 are stably pushed into the position in which the pin 25 is engaged in the hole 24 against the action of the spring 27, by another spring 32. Hence, the lever 30 need only be driven to disengage the locking pin 25 from the hole 24, in order to unlock the footrest 20 from the operating position, and to bring it into the inwardly turned idle position, against the legs 302.

The figures show another characteristic, consisting in that the plane 102 of the examination table 2 has several cavities, recesses or niches, both on its ends and sides. These hollows are indicated as 35, 36 and handle elements 33 are fastened thereat. The handle elements 33 and the niches 35, 36 are so shaped that the former may be easily and comfortably grasped, although they do not protrude or project out of the space occupied by the plane 102, unless to an insignificant extent.

FIGS. 2 and 3 and 4 and 5 show the potentialities and functions of the examination table according to the invention.

Figure 2:
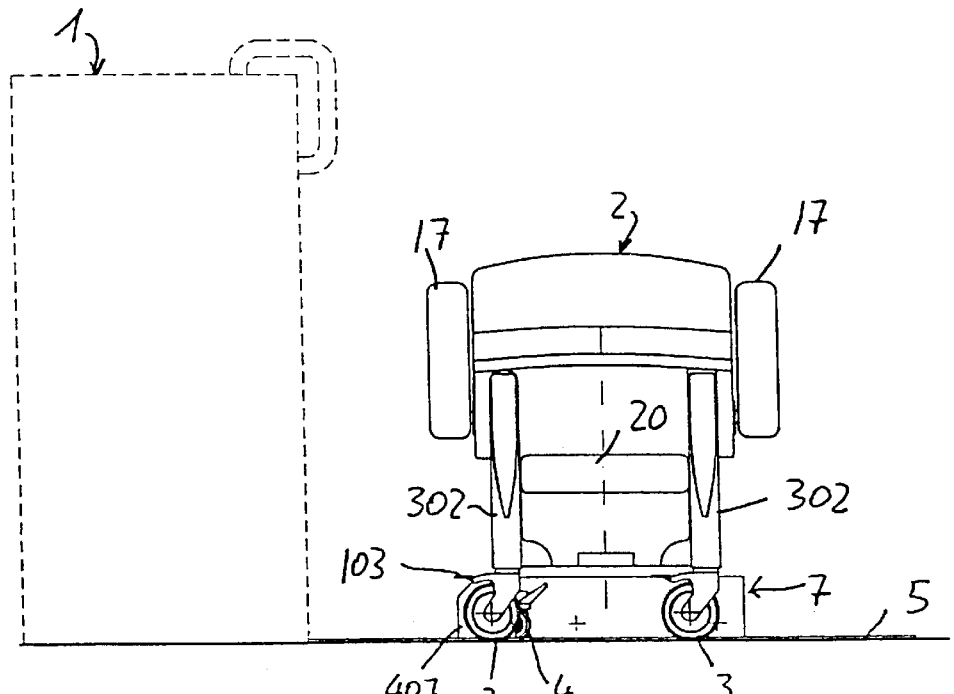
FIGS. 2 and 3 are elevational and plan views respectively of the machine according to FIG. 1, with the examination table rotated to a position perpendicular to the direction of insertion/extraction of the body part in and from the detection cavity.
Figure 3:
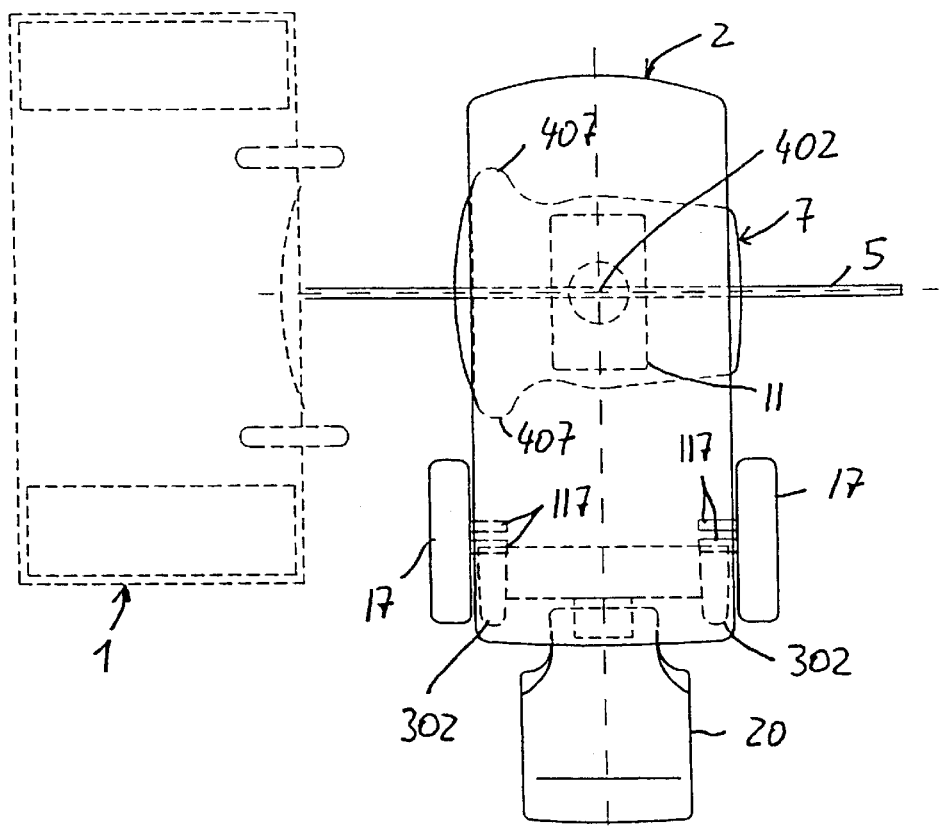
Figure 4:
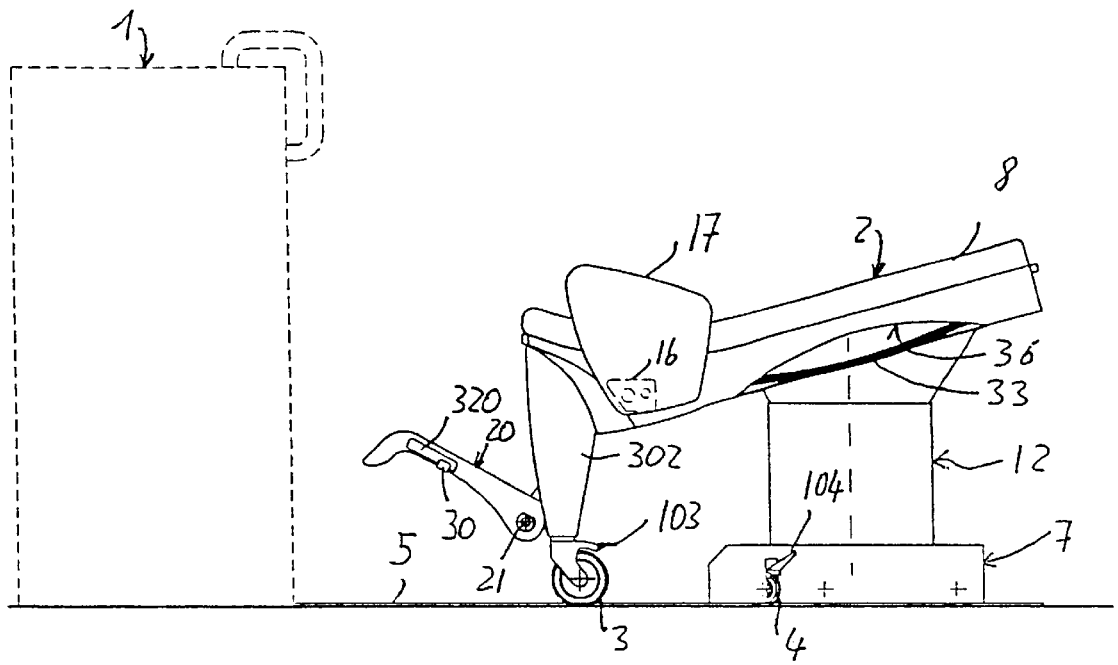
FIGS. 4 and 5 are views like those shown in FIGS. 2 and 3, of the machine according to FIG. 1, with the examination table oriented parallel to the direction of insertion/extraction of the body part to be examined in and from the detection cavity.
Figure 5:
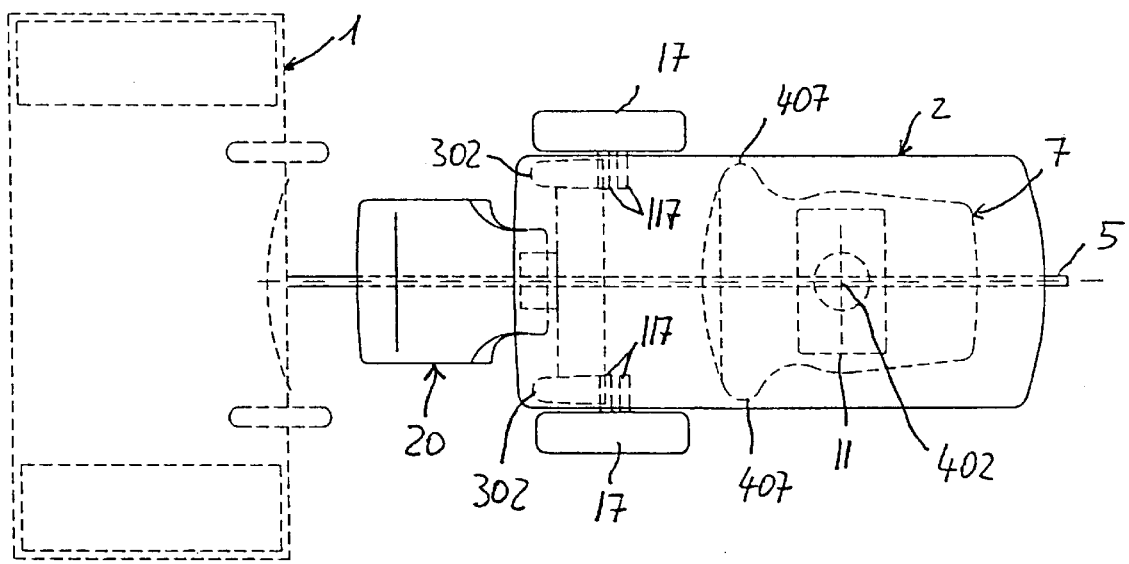

In FIGS. 2 and 3, the examination table is oriented transverse, particularly perpendicular to the axis of the detection cavity 101, and hence of the translation guide 5. In this position, the footrest 20 may be set in any position, as the patient desires. This arrangement of the examination table is particularly recommended for the treatment of arms and hands. In this case, part of the patient body comfortably lays on the examination table, whereas the arm to be treated, or the one associated to the hand to be treated, is outwardly oriented, in the natural position in which it is held out transverse to the body, which position is also substantially on the same axis as the detection cavity 101. So, the patient takes a perfectly comfortable position, corresponding to the functional characteristics of the limb. In this way, he can more easily keep his limb relaxed and still during the image detection process. The introduction and the extraction of the arm into and from the detection cavity 101 is simply obtained by translating the examination table 2 along the guide 5. Thanks to the fact that the examination table 2 may be rotated about the vertical axis 402, the orientation of the examination table 2 may be adjusted with respect to that of the detection cavity 101 without interruption and in such a way as to obtain the best patient positioning.

In order to detect images of one leg or parts thereof, the examination table 2 is rotated until its longitudinal axis takes a position substantially parallel to the axis of the detection cavity 101. In this position, the patient, on the examination table 2 is oriented in such a way that his legs are substantially aligned with the detection cavity 101. The leg is introduced in the correct position into the detection cavity 101 and extracted therefrom, by a translation movement along the guide 5. This case also provides that the examination table 2 may be angularly displaced to be adjusted with respect to the axis of the detection cavity 101.

According to the extent whereto a leg is inserted into the detection cavity 101, the footrest 20 is in the operating position, or turned to the idle position. As a rule, the footrest 20 may be kept in the operating position when a foot or a heel are to be examined. Conversely, when images of a knee are to be detected, the footrest is to be brought to the idle position, so that the examination table may be further approached to the opening of the detection cavity 101.

Naturally, the invention is not limited to the embodiments described and illustrated herein, but may be varied, especially as regards construction, without departure from the guiding principle disclosed above and claimed below.

What is claimed is:

1. A method of imaging a part of a body with a Nuclear Magnetic Resonance image forming machine designed for forming images of only parts of a body, in combination with an examination table, wherein there is a guide for moving the examination table to and from the machine in a line, and wherein the examination table is able to rotate along a vertical rotational axis, the method comprising the steps of:

arranging a patient on the table so that the part of the body to be imaged extends off of the table;

orienting the table about the vertical rotational axis so that the part of the body to be imaged extends along the line;

moving the table toward the machine until the part of the body to be imaged is in a detection cavity of the machine and while all of the table is outside of the detection cavity; and forming an image of the part of the body with the machine.

2. The method of claim 1, further comprising the step of fixing a hinged footrest in a vertical position for forming an image of a leg part.

3. A method as in claim 2, wherein said fixing of the footrest in a vertical position comprises:

turning the footrest about a horizontal axis at an end of the table.

4. A method as in claim 3, wherein said fixing of the footrest in a vertical position comprises:

positioning the footrest within a cavity at the end of the table.

5. The method of claim 1, further comprising the step of fixing a hinged footrest in a horizontal position for forming an image of a part of the body other than a leg or foot part.

6. A method as in claim 5, wherein said fixing of the footrest in a horizontal position comprises:

turning the footrest about a horizontal axis at an end of the table.

7. A method as in claim 6, comprising:

adjusting a height of the footrest prior to said fixing of the footrest in the horizontal position.

8. A method as in claim 6, wherein said fixing of the footrest in a horizontal position comprises:

locking said footrest into the horizontal position in a lateral guide, wherein lateral guide is attached to a leg of the table.

9. The method of claim 1, further comprising the step of resting an arm of the body on an armrest attached to the examination table.

10. A method as in claim 1, wherein said moving the table toward the machine comprises:

sliding a roller of the examination table on a translational guide in a direction parallel to a central axis of the detection cavity.

11. A method as in claim 10, wherein said moving the table toward the machine comprises:

rolling a wheel of the examination table in a direction parallel to a central axis of the detection cavity.

* * * * *

UNITED STATES PATENT AND TRADEMARK OFFICE
CERTIFICATE OF CORRECTION

PATENT NO. : 6,374,133 B1
APPLICATION NO. : 09/986169
DATED : April 16, 2002
INVENTOR(S) : Orfeo Contrada et al.

It is certified that error appears in the above-identified patent and that said Letters Patent is hereby corrected as shown below:

Title page item 73 under Assignee, please insert --Esaote S.p.A., Monferrato (AL), ITALY--

Signed and Sealed this

Twentieth Day of February, 2007

JON W. DUDAS
*Director of the United States Patent and Trademark Office*